US 6,719,731 B2

(12) United States Patent
Parmigiani

(10) Patent No.: US 6,719,731 B2
(45) Date of Patent: Apr. 13, 2004

(54) PROTECTION DEVICE FOR MEDICAL NEEDLES

(75) Inventor: Corrado Saverio Parmigiani, Correggio (IT)

(73) Assignee: C.G.M. S.p.A., Correggio (IT)

( * ) Notice: Subject to any disclaimer, the term of this patent is extended or adjusted under 35 U.S.C. 154(b) by 0 days.

(21) Appl. No.: 09/878,264

(22) Filed: Jun. 12, 2001

(65) Prior Publication Data

US 2001/0053892 A1 Dec. 20, 2001

(30) Foreign Application Priority Data

Jun. 12, 2000 (IT) ...................................... RE2000A0064

(51) Int. Cl.[7] .............................. A61M 5/32; A61M 5/00
(52) U.S. Cl. ...................... 604/192; 604/198; 604/177; 604/263
(58) Field of Search .......................... 604/263, 192–198, 604/162, 110, 177

(56) References Cited

U.S. PATENT DOCUMENTS

| 4,935,013 A | | 6/1990 | Haber et al. | |
|---|---|---|---|---|
| 5,112,311 A | * | 5/1992 | Utterberg et al. | 604/177 |
| 5,192,275 A | * | 3/1993 | Burns | 604/177 |
| 5,382,240 A | * | 1/1995 | Lam | 604/110 |
| 5,746,215 A | * | 5/1998 | Manjarrez | 600/573 |
| 5,951,525 A | * | 9/1999 | Thorne et al. | 604/162 |

FOREIGN PATENT DOCUMENTS

EP          0 534 000 A2      3/1993

* cited by examiner

Primary Examiner—LoAn H. Thanh
Assistant Examiner—Roz Maiorino
(74) Attorney, Agent, or Firm—Browdy and Neimark, P.L.L.C.

(57) ABSTRACT

A protection device for medical needles connected to a portion of tube comprises: a protection casing (20) arranged to enclose and cover the needle after use, it being initially applied in a position to the rear of the point (11) of the needle; a front end (25) facing the point of the needle, to be rested against a foreign body (D3) for reaction in extracting the needle from the patient's body; means (30) for securing the device to the tube (15); and thrust means (21, 22) which when operated by the operator's finger (D1, D2) increase the distance between the securing means (30) and said front end (25) in order to cause the needle (10) to move towards the protection casing (20) until it lies inside the interior of this latter (20). During the extraction of the needle (10) from the patient's body (P), the device (1) is rigidly secured to the tube (15) in proximity to the needle (10), and the operator, by operating on the device, is able to direct the needle (10) as he wishes, to achieve its correct extraction.

9 Claims, 6 Drawing Sheets

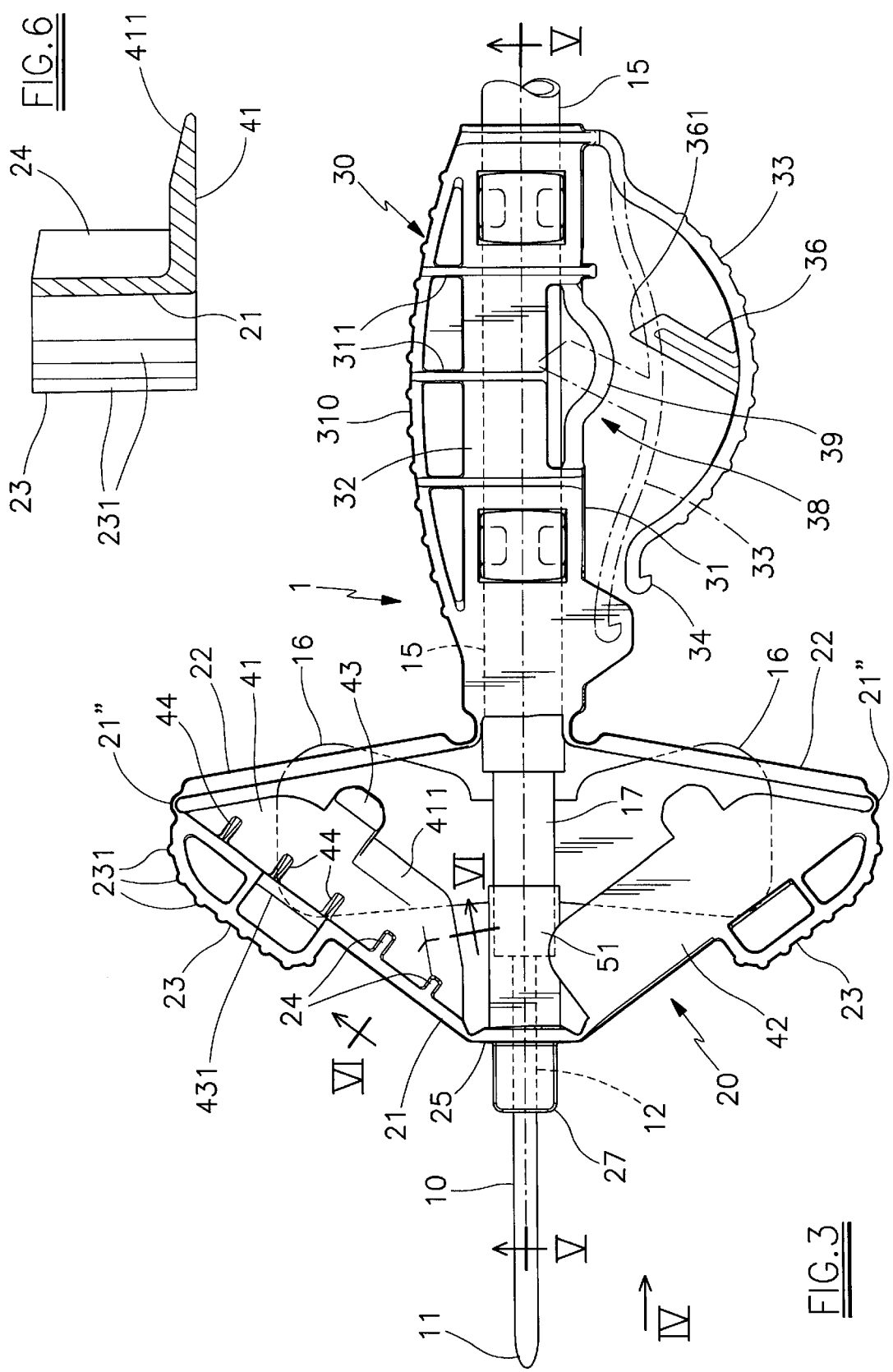

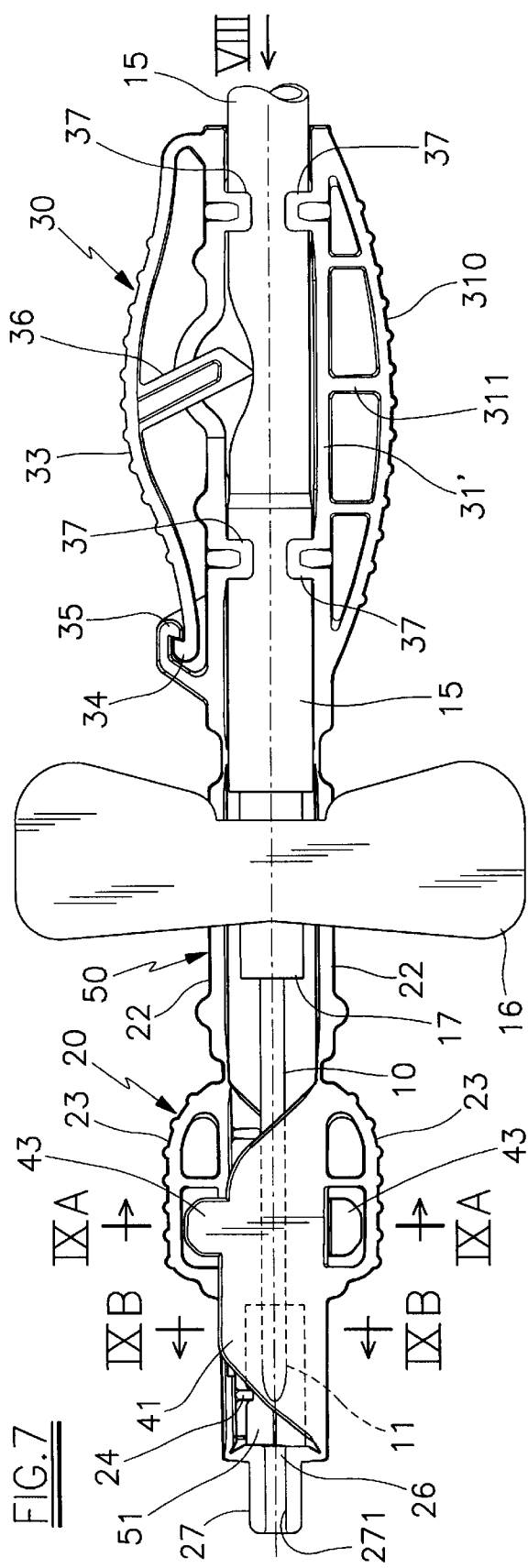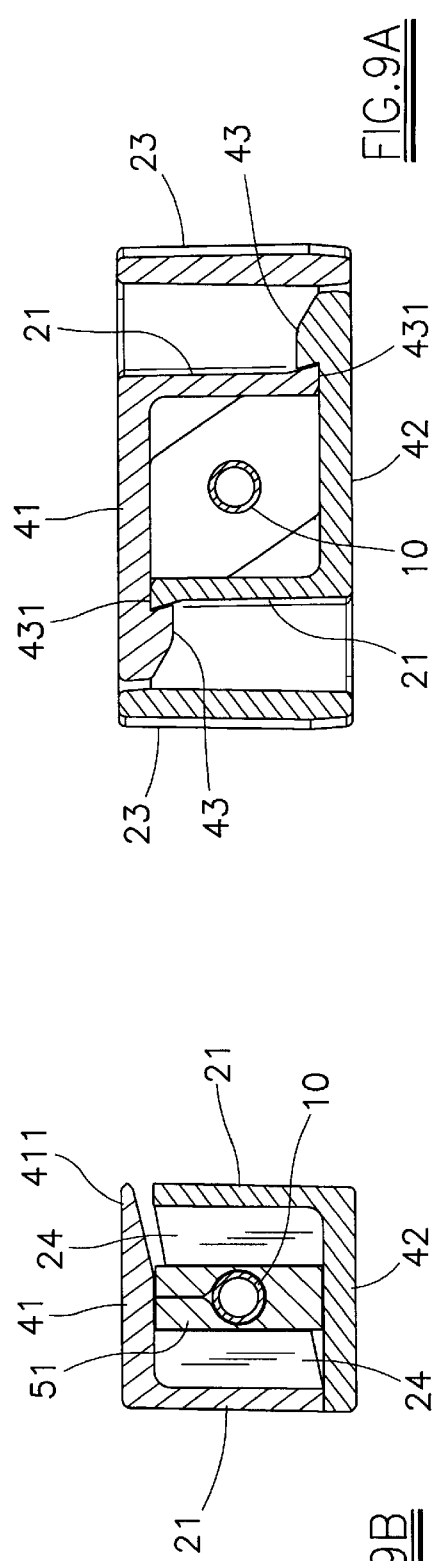

PROTECTION DEVICE FOR MEDICAL NEEDLES

BACKGROUND OF THE INVENTION

1. Technical Field of the Invention

This invention relates to a protection device for medical needles connected to a portion of tube, to prevent accidental pricking after using the needle. The field of application includes needles for infusion, for dialysis or plasmapheresis, for transfusions and for sampling.

2. Prior Art

Pricking by medical needles after their use on a patient represents a serious and widespread risk for personnel operating in the health sector.

To solve this problem protection devices are known comprising substantially a tubular casing coaxial to the tube to which the needle is connected, and having a hook-shaped front projection by which the device is retained by a finger of the hand which is pressed against the surface of the patient, at the point in which the needle is inserted into the patient's body.

The needle is extracted from the patient's body by pulling the tube rearwards; this operation causes the needle to withdraw while the protection device is held still by the finger, with the result that the needle slides under the projection and is retracted into the interior of the tubular casing, where its point is enclosed and protected against contact with external bodies.

As the device is applied to needles of the type having two fins positioned close to the rear end (butterfly needles), the tubular casing possesses two longitudinal slits in its lateral walls for passage of the fins.

OBJECT AND SUMMARY OF THE INVENTION

An object of the present invention is to overcome those drawbacks of known devices, in particular with regard to the dangers involved in extracting the needle from the patient's body. In this respect, this operation is delicate in itself, even without the protection device being present, because in many cases the needle point has a cutting edge and can damage the patient. The fact that the operator has to retain the protection device while at the same time making the extraction by gripping the tube at a point relatively far from the needle, makes the operation even more difficult and risky because of the danger of cutting the patient, in particular at the point of penetration of the needle.

Another drawback lies in the low rigidity of the tubular casing, particularly because of the presence of the longitudinal slits, and which in general means that it is impossible to ensure that the point of the needle is properly enclosed, secured and protected.

As stated, one object of the present invention is to overcome said drawbacks.

Another object is to provide a device which can be applied to the needle when this is already inserted into the patient's body, just before the needle is to be extracted.

These and further objects are attained by the device of the invention as characterised in the claims.

The invention is based on the fact of comprising: a protection casing arranged to enclose and cover the needle after use, it being initially applied in a position to the rear of the point of the needle; a front end facing the point of the needle, to be rested against a foreign body for reaction in extracting the needle from the patient's body; means for securing the device to the tube; and thrust means which when operated by the operator's finger increase the distance between the securing means and said front end in order to cause the needle to move towards the protection casing until it lies inside the interior of this latter.

In particular, the device comprises a rear portion connected to the rear of the protection casing and carrying the means for securing the device, said front end being defined by the front end of the protection casing.

The protection casing is of such a shape as to enable it to vary its dimension in the longitudinal direction, said thrust means acting to produce an increase in the longitudinal dimension and consequently in the distance between the rear portion and the front end of the protection casing. In particular, the protection casing comprises initially diverging opposing lateral walls which can be made to approach each other to produce said increase in the distance between said rear portion and the front end of the protection casing.

BRIEF DESCRIPTION OF THE DRAWINGS

The invention is described in detail hereinafter with the aid of the accompanying figures which illustrate one embodiment thereof by way of non-limiting example.

FIG. 3 is a plan view from above showing the device of FIG. 1 applied to a butterfly needle.

FIG. 6 is a section on the plane VI—VI of FIG. 3.

FIG. 7 is a plan view from below showing the said device in its closed configuration.

FIGS. 9A and 9B are sections on the plane IXA—IXA and respectively IXB—IXB of FIG. 7 on an enlarged scale.

DETAILED DESCRIPTION OF THE PREFERRED EMBODIMENTS OF THE INVENTION

Figure 1:
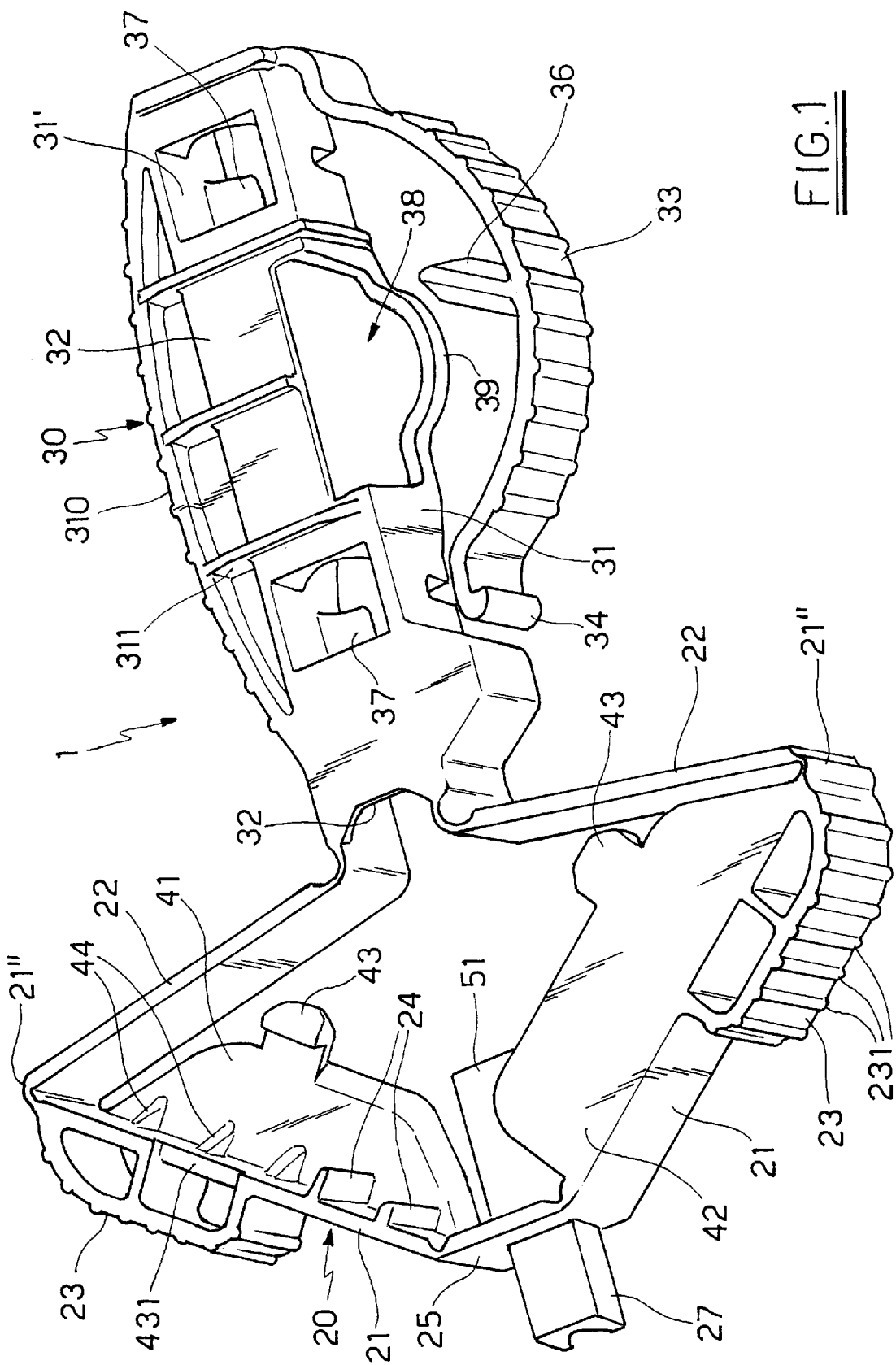
FIG. 1 is a perspective view of the device of the invention taken from the upper side.

The device is applied to a medical needle 10, formed from a thin tubular element 12 having a front point 11 arranged to penetrate into the patient's body; the needle 10 is connected at its rear to a flexible tube 15. The needle shown in the figures is of the butterfly type, i.e. it comprises a pair of flexible fins 16 positioned in the same plane and joined by a support sleeve 17 to the rear portion of the tubular element 12.

For greater simplicity and clarity of description, it will be assumed, as spatial reference, that the ideal plane tangential to the surface of the patient's body at the point in which the needle is inserted is horizontal.

The device of the invention (indicated overall by 1) comprises a protection casing 20 arranged to enclose and cover the needle 10 after use, and in particular arranged to enclose its point 11.

The device also comprises a front end 25 facing towards the needle point 11 and defined specifically by the front end of the protection casing 20, to be rested against an external body (in particular against a finger of the operator's hand) acting as a reaction body for extracting the needle 10 from the patient's body.

The device 1 also presents a rear portion 30 joined to the rear of the protection casing 20 and coaxial therewith, and carrying the means for securing the device 1 to the tube 15.

In particular, the rear portion 30 is of substantially tubular shape, defining an axial channel able to contain as an exact fit a corresponding portion of tube. In detail, the portion 30 comprises two mutually parallel opposing vertical lateral walls 31 and 31' and a horizontal upper wall 32, which define an axial channel of substantially square cross-section and of dimensions such as to contain the tube 15 virtually as an exact fit or with slight forcing.

This channel is open on its lower face, to enable this rear portion 30 to be positioned over and about the tube 15 by being moved transversely from above downwards.

Said securing means comprise a snap-engaging element comprising a projecting blade 33 associated with a lateral wall 31 of the rear portion 30, to which a transversely projecting part 36 is connected, to be pushed into the channel defined by the rear portion 30 in order to lock the tube 15 inside this channel when the engagement element 33 is moved into its engaged configuration.

The projecting blade 33 is positioned on the outside of and parallel to the wall 31 joined by its rear end to the rear end of the wall 31. The blade 33 is bent as an arch with its concavity facing the wall 31, and is elastically yieldable in a horizontal plane (i.e. parallel to the surface of the patient's body). The free end of the blade 33 is shaped in the form of a tooth 34 to be coupled to a corresponding coupling tooth 35 positioned on said wall 31.

Normally, the two teeth 34 and 35 are separated and relatively distant from each other and the blade 33 has a relatively small radius of curvature; in this configuration, the part 36 does not interfere with the tube 15 positioned in the channel of the portion 30, which is therefore not firmly secured to the portion 30.

Advantageously, the entire device 1, and in particular the rear portion 30 and the securing means, are formed in one piece from rigid but sufficiently elastic synthetic resin.

To secure the tube 15 to the portion 30, the blade 33 is pressed in a horizontal transverse direction to cause it to approach the wall 31 so that it deforms in the sense of increasing its radius of curvature, until the two teeth 34 and 35 are brought into mutual engagement. When in this configuration, the projecting part 36 has penetrated transversely into the channel of the portion 30, where it presses strongly against the tube 15, to press it against the opposing wall 31' and also against the upper wall 32, in order to securely lock the tube 15 and make it rigid with the portion 30.

This action is accomplished by squeezing together two fingers of one hand, one acting against the blade 33 and the other against the opposing wall 31'.

The part 36 penetrates into the channel of the portion 30, through an ample aperture 38 provided in the wall 31. Preferably, the part 36 acts pointwise against the tube 15, by means of a front wall 361 which is slightly inclined forwards and downwards; by reaction, the part 36 receives from the tube 15 a transverse trust having a downwardly directed component; to oppose this component, the lower surface of the part 36 rests on a lower longitudinal element 39, connected at both ends to the wall 31 and extending along the aperture 38 from side to side.

To stiffen the wall 31' in order to make it more resistant to radial thrusts, in the embodiment shown in the figures there is provided an arched lateral reinforcement wall 310 positioned external to the wall 31' and joined thereto by its ends and by transverse ribs 311.

In addition, to facilitate the action of the fingers which press the blade 33, various light projections are provided on the outer surfaces of the wall 310 and blade 33 to make said surfaces non-slippery.

Light projections 37 are also preferably provided extending transversely from the lower edge of the walls 31 and 31' to at least slightly secure the tube 15 against its escape from the lower end of the portion 30, they being overcome snap-wise by the tube 15 when this is inserted into the channel of the portion 30, by virtue of the flexibility of the tube.

Joined to the front of the rear portion 30 there is the protection casing 20 for enclosing and protecting the needle, it being formed of synthetic resin in one piece with the rear portion 30.

The protection casing 20 is of such a shape that its dimension in the longitudinal direction can be varied.

In particular, it comprises a pair of swivelling front lateral walls 21 and a pair of swivelling rear walls 22, all vertical, mutually opposing and initially diverging, they being able to be moved towards each other to produce an increase in the distance between the rear portion 30 and the front end 25 of the casing 20.

Each front lateral wall 21 is hinged at its front end to the front end, in the form of a vertical front wall, of the casing 20 and is hinged at its other end to the front end of a respective rear lateral wall 22. The rear walls 22 connect to the rear portion 30 to which they are hinged at their rear end. In short, the four walls 21 and 22 form an articulated quadrilateral in which, by moving the rear ends 21" of the two front lateral walls 21 towards each other (and coinciding with the front ends of the rear walls 22), the quadrilateral is squashed with consequent increase in the distance between the rear portion 30 and the front end 25 of the protection casing 20.

The mutual hinging regions between the walls 21 and 22 and between these and the front end 25 and rear portion 30 are in the form of thin sheet metal parts integral with the entire device 1.

The four walls 21 and 22 define thrust means arranged to increase, when operated by the operator's fingers, the distance between the rear portion 30 (and hence the securing means) and the front end 25, to cause the needle to move towards the protection casing 20 until it lies in the interior of this latter.

To facilitate the action of the fingers which press on the articulated quadrilateral, two projecting elements 23 particularly suitable for receiving the applied thrust by the two fingers are provided, they comprising various light projections 231 to make the surfaces on which the fingers rest non-slippery.

In their initial configuration, the front walls 21 (and also the rear walls) are diverged apart to the maximum extent and the elements 23 are at their maximum distance apart (as shown in FIG. 3); whereas when in their final configuration, after use, the front walls 21 (and also the rear walls) are close together and mutually parallel, with the elements 23 at their minimum distance apart (as shown in FIG. 7).

The front part of the protection casing 20 defines a tubular portion 40 arranged specifically to enclose the needle when the front walls 21 are moved towards each other (and the needle is withdrawn into the tubular portion).

Said portion 40 comprises the two opposing front walls 21 and cover means for enclosing and covering the needle, together with the walls 21 themselves, when these are made to approach each other. The two front lateral walls 21 mutually swivel in the plane tangential to the patient's body, to approach each other, and are disposed vertically to said tangential plane, said cover means comprising at least two flat horizontal elements 41 and 42 arranged to close the lower and upper horizontal surfaces of the tubular portion 40 when the two lateral walls 21 are parallel and close to each other.

The flat element 41 as positioned on the lower side of the protection casing 20 (i.e. on that side which comes into contact with the patient's body), to adhere to and slide on the surface of the patient below the needle 10 when this is inserted into the patient's body, in order to collect the needle and bring it into the chamber of the tubular portion. For this purpose the element 41 possesses a flat lower surface which remains adhering to the surface of the patient's body, and an end edge 411 facing the interior of the chamber and positioned close to the front end 25, it being of pointed section to enable it to be more easily inserted below the needle 10.

Said flat elements 41 and 42 project horizontally from a respective side wall 21 and present at their free end a tooth 43 arranged to snap-engage the opposing lateral wall 21, in particular in a suitable seat 431 formed as a depression in the upper edge of the wall 21. A number of flat triangular elements 44 lying in planes perpendicular to the corner defined by the elements 41, 42 and the wall 21 are joined to each flat element 41, 42 and to the relative lateral wall 21 to reinforce the structure.

The front face of the tubular portion 40 is closed by the front wall which defines the front end 25.

Said front wall 25 presents in its lower side an aperture 26 which comes into contact with the patient's body and allows the needle 10 to pass.

When the device is in its closed configuration (see FIG. 7 in particular) to the rear of the tubular portion 40, the protection casing 20 comprises a rear section 50 defined by the two rear lateral walls 22 positioned parallel to each other; said rear section 50 is arranged to contain the end rear portion of the tubular element 12 of the needle 10 and the sleeve 17, its lower face being open so that the (possible) fins of the needle are disposed external to and below said rear section 50.

The device 1 is used in the manner described hereinafter with the aid of FIG. 10, which schematically illustrates a typical manner of using the device.

The device 1 is used in the case of needles inserted into the body P of the patient (in FIG. 10 the needle is inserted into an arm of the patient) in a direction nearly parallel to the surface of the body P; in such cases the rear end portion of the needle 10, which remains outside, lies substantially resting on the surface of the patient, by virtue of tissue elasticity.

If the needle is provided with fins 16, as illustrated in the figures, these fins are rested on the surface of the patient's body P.

Figure 2:
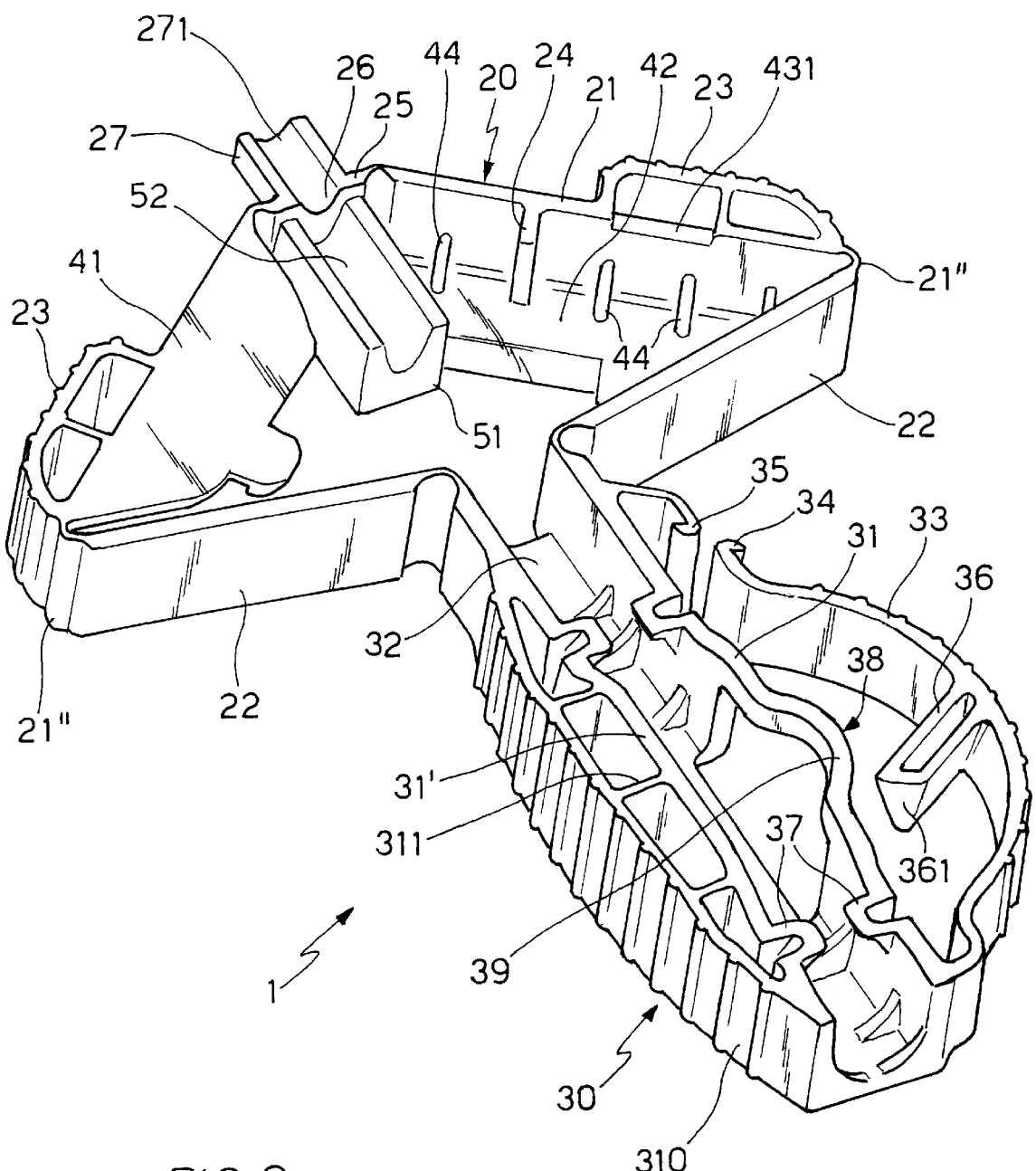
FIG. 2 is a perspective view of the device of the invention taken from the lower side.
Figure 8:
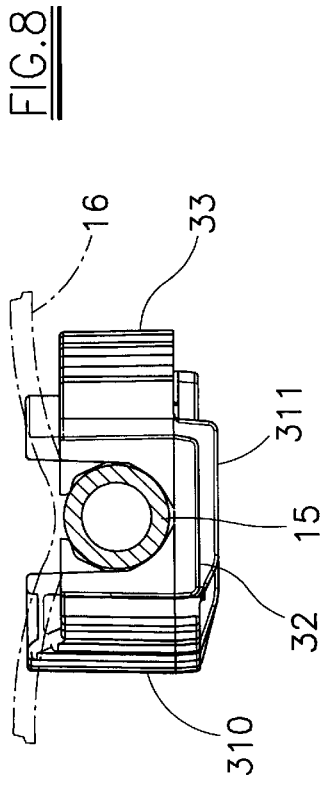
FIG. 8 is a vertical front elevation in the direction VIII of FIG. 7.
Figure 4:
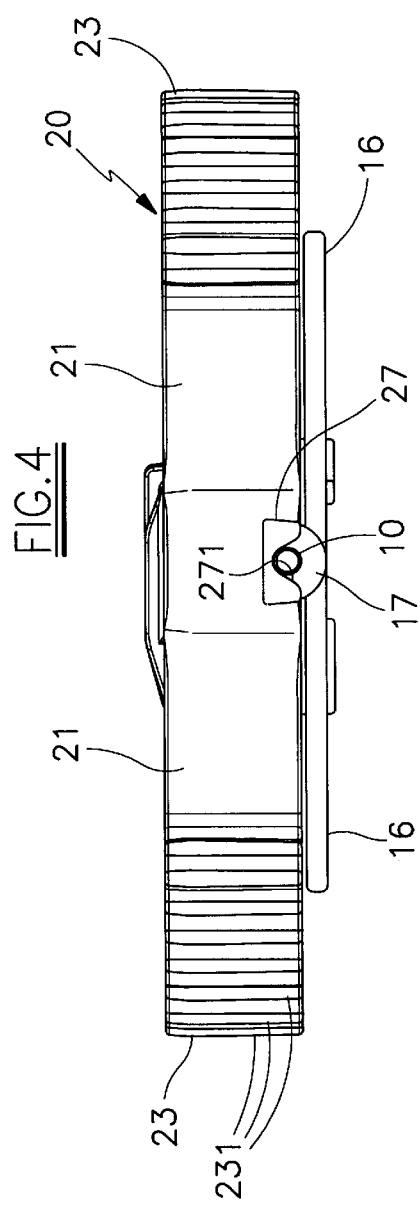
FIG. 4 is a vertical front elevation in the direction IV of FIG. 3.
Figure 5:
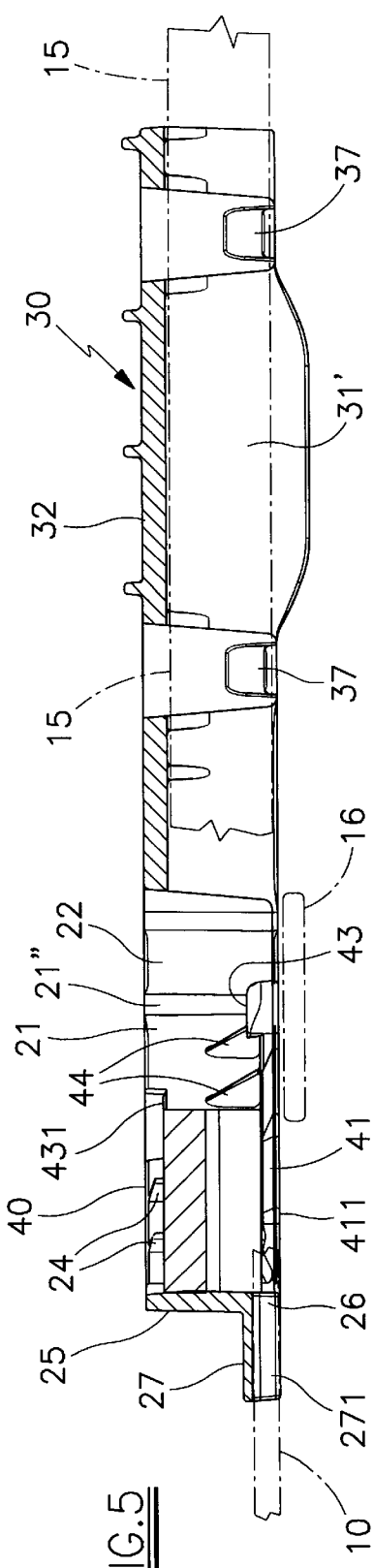
FIG. 5 is a section on the plane V—V of FIG. 3.

The device 1 is firstly applied to the tube 15 from above, by positioning the rear portion 30 straddling the tube 15, then with a downward vertical movement inserting the tube 15 into the channel defined by the rear portion 30, via its open rear face. For correct initial application, the aperture 26 in the front end 25 is positioned on the rear portion of and external to the needle 10, in front of the sleeve 17, with the walls 21 and 22 in their configuration of maximum divergence (as shown in FIGS. 1–3). When in said configuration the walls 21 and 22 lie on the fins 16.

At this point, by pressing on the element 33 and on the opposite wall 33 with two fingers D1 and D2 to produce opposing transverse thrusts, the teeth 34 and 35 are mutually engaged and the tube is securely fixed to the rear portion 30.

Figure 10:
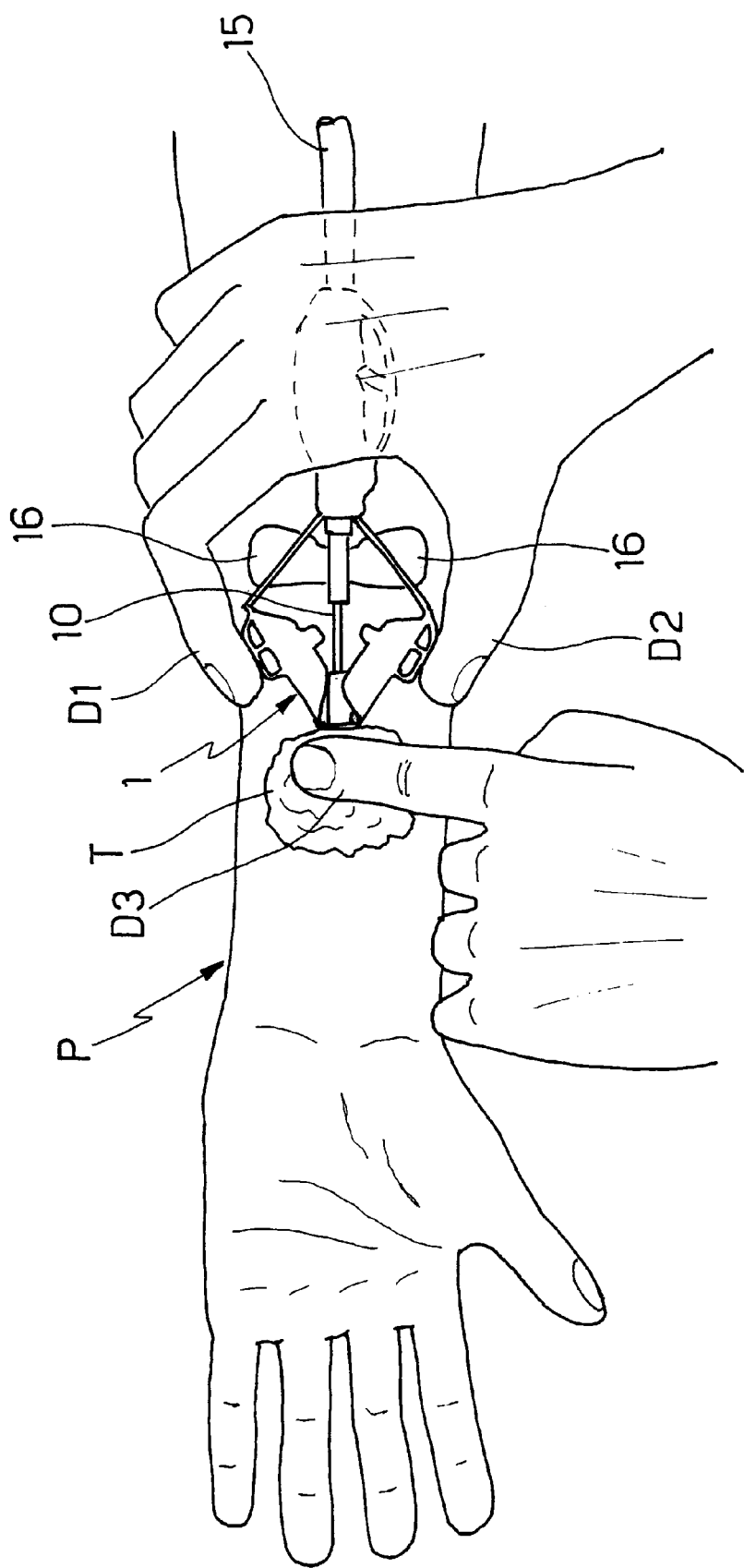
FIG. 10 is a schematic view showing the use of the device.

Then (as shown in FIG. 10) thrust action is applied to the casing 20 by said fingers D1 and D2 applied to the two elements 23, to produce opposing transverse (horizontal) thrusts directed in the sense of moving said elements 23 towards each other. This action is applied while a third finger D3 of the operator presses, as is usual, a pad T (for example of cotton) against the patient's body P at the point in which the needle 10 penetrates the body. While the action of the two fingers D1 and D2 on the two elements 23 is squeezing the quadrilateral formed by the walls 21 and 22, the front end 25 thereof immediately, or after a short distance, comes into contact with the third finger D3, where it halts and by reaction causes the rear portion 30 to move rearwards and with it the tube 15 and the needle 10. The result is that the needle is pulled rearwards, withdrawing below the third finger D3, until it, together with its point, completely enters the tubular portion 40, by sliding in contact with the surface of the body P and sliding below the aperture 26. In the meantime, the sleeve 17 becomes housed within the rear section 50.

During the lengthening/squeezing of the protection casing 20, the walls 21 approach each other (as do simultaneously the rear walls 22) and the portion 40 assumes an increasingly tubular shape. The rear lateral walls 22 slide in contact with the upper surface of the fins 16; the front lateral walls 21 and the element 41 themselves slide along the patient's body P. The flat element 41 slides under the needle 10 while this is extracted, and urges it upwards to pull it into the tubular portion 40. The triangular elements 44 also act on the needle 10 when the portion 40 is closed, to position it along or near the longitudinal axis of the casing.

On termination of the operation, the needle 10 lies virtually completely within the tubular portion 40, enclosed by the walls 21, by the front end 25 and by the flat elements 41 and 42. These latter are also coupled to the walls 21 to hence give rise to a truly solid box structure closed firmly and securely (see FIG. 9 in particular). The fins 16 however always remain outside the protection casing 20, below the rear walls 22. At the same time, the entire device is fixed to the tube 15 by the securing means of the rear portion 30.

When in this configuration, the device 1 effectively encloses the needle 10 and prevents this being able to prick any person.

In the preferred embodiment shown in the figures, a flat element 27 is provided projecting forwards from the front wall 25, to cover the region in front of the needle passage aperture. This element 27 presents in its lower surface an axial groove 271, positioned as a continuation of the aperture 26, to house a portion of the needle 10.

When in use, the operator positions this front wall 25 above the point at which the needle 10 penetrates into the patient's body P, with possibly a suitable pad T interposed between the surface and the element 27; he then presses with his third finger D3 on the element 27. In this case, said third finger D3 is better protected against possible cuts or pricks produced by the point 11 of the needle while this is being pulled out of the patient's body.

In the preferred embodiment shown in the figures, there is also provided a sponge piece 51 connected to the tubular portion 40, to wrap the point 11 of the needle when this is withdrawn into the tubular portion. In particular, said sponge piece 51 is applied to the front wall 25 and possesses a groove 52 positioned axially to the needle passage aperture 26, to house the needle point. In detail, the piece 51 is of parallelepiped shape, its lower face making contact with the surface of the patient when the device 1 is applied to the tube 15; the groove 52 is provided in this lower face as a continuation of the groove 271 on the outside of the tubular portion. When in use, the sponge piece 51 is compressed in the transverse direction by the front lateral walls 21 when these are made to approach each other, until it encloses the point 11 of the needle within its spongy mass. To effectively compress the piece 51, a number of vertical transverse projections 24 are provided, joined to the front lateral walls 21 and to the relative flat element 41, 42, and projecting towards the interior of the tubular portion 40 (see FIG. 9B in particular), such that when the tubular portion 40 attains the final closed configuration, they compress the piece 51 with their free vertical edge and squeeze it to the extent that its mass closes about the needle 10 and wraps it completely.

The action of the sponge piece serves mainly to cover the point of the needle in contact with it after the needle has been extracted, so that the blood or other liquids present on its surface become incorporated into the sponge piece to prevent these substances separating from the needle and possibly coming into contact with objects or persons.

One of the advantages of the invention is that, during the extraction of the needle 10 from the patient's body P, the device 1 is rigidly secured to the tube 15 in proximity to the needle 10, and the operator, by operating on the device, is able to direct the needle as he wishes, to achieve its correct extraction. The presence of the rear portion 30 acts as a sort of handgrip for the hand which presses against the two elements 23.

Numerous modifications of a practical and applicational nature can be made to the device of the invention, but without leaving the scope of the inventive idea as claimed below.

What is claimed is:

1. A protection device for a medical needle connected to a portion of a tube, comprising:
    a protection casing (20) adapted to engage and cover the needle after use, the protection casing being initially applied in a position to a rear of a point (11) of the needle;
    a front end (25) of the protection casing adapted to face the point of the needle when extracting the needle from a patient's body;
    a rear portion (30) engaged with the protection casing having securing means for securing the device to the tube (15) during extraction of the needle;
    thrust means on the protection casing for increasing a distance between the securing means and said front end (25) to move the needle into an interior of the protection casing during extraction of the needle,
    wherein said front end (25) has a groove in a lower side of the protection casing allowing passage of the needle, and the rear portion is open on a lower face thereof, to enable the rear portion to be positioned over and about the tube and against the patient's body, and
    wherein the protection casing (20) comprises diverging opposing lateral walls (21, 22) compressable towards each other to produce an increase in a longitudinal dimension and consequently in a distance between the rear portion and the front end of the protection casing, and cover means which define, together with the opposing lateral walls, a tubular portion for enclosing and covering the needle (10), when said lateral walls are compressed towards each other.

2. The device according to claim 1, wherein said cover means comprises at least one flat element adapted to be positioned on a side of the protection casing which is placed in contact with a patient's body, to engage and slide on a surface of the patient's body under the needle (10), so that the needle (10) is brought into a chamber of the tubular portion (40).

3. The device according to claim 2, wherein the flat element has a flat lower surface adapted to engage the surface of the patient's body, and an edge facing an interior of the chamber, positioned close to the front end of the protection casing and having a pointed edge to enable easy insertion below the needle.

4. The device according to claim 2, wherein the flat element projects horizontally from a respective lateral wall (21) and has a tooth at a free end thereof arranged to engage an opposing lateral wall (21).

5. The device according to claim 2, wherein the tubular portion (40) has two opposing front lateral walls (21) hinged to said front end (25), and hinged to two opposing rear lateral walls (22) hinged to the rear portion (30) to form an articulated quadrilateral in which, by compressing the rear ends of the two opposing front lateral walls (21) towards each other, the distance between the rear portion (30) and the front end (25) of the protection casing (20) is increased, the protection casing (20) having at a rear of the tubular portion (40), a rear section (50) which has an open lower face arranged to contain a end rear portion of the needle, fins of the needle being disposed external to and below said rear section (50).

6. The device according to claim 5, wherein said securing means has a snap-engaging element (33) associated with said rear portion (30), to which a transversely projecting part (36) is connected, to be pushed into a channel defined by the rear portion (30) to lock the tube (15) positioned inside the channel when the engagement element (33) is moved into an engaged configuration.

7. The device according to claim 5 further comprising a sponge piece (51) connected to the tubular portion (40), to wrap the point (11) of the needle when withdrawn into the tubular portion (40).

8. The device according to claim 6, wherein said sponge piece (51) is engaged to the front wall (25) and has a groove (52) positioned axially to a needle passage aperture (26) so as to house the point (11) of the needle, said sponge piece (51) being compressed transversely by the two opposing front lateral walls (21) when compressed to approach each other, until the point (11) of the needle is enclosed within a mass of the spongy piece.

9. A protection device for a medical needle connected to a portion of a tube, comprising:
    a protection casing (20) adapted to engage and cover the needle after use, the protection casing being initially applied in a position to a rear of a point (11) of the needle;
    a front end (25) of the protection casing adapted to face the point of the needle when extracting the needle from a patient's body;
    a rear portion (30) engaged with the protection casing having securing means for securing the device to the tube (15) during extraction of the needle;

thrust means on the protection casing for increasing a distance between the securing means and said front end (25) to move the needle into an interior of the protection casing during extraction of the needle, wherein said front end (25) has a groove in a lower side of the protection casing allowing passage of the needle, and the rear portion is open on a lower face thereof, to enable the rear portion to be positioned over and about the tube and against the patient's body, wherein said rear portion is of a substantially tubular form, defining a channel arranged to contain as an exact fit a corresponding portion of the tube (15).

* * * * *